United States Patent [19]

Shah

[11] Patent Number: 4,892,742

[45] Date of Patent: Jan. 9, 1990

[54] CONTROLLED RELEASE COMPOSITIONS WITH ZERO ORDER RELEASE

[75] Inventor: Navnit H. Shah, Clifton, N.J.

[73] Assignee: Hoffmann-La Roche Inc., Nutley, N.J.

[21] Appl. No.: 799,229

[22] Filed: Nov. 18, 1985

[51] Int. Cl.$^4$ ............................................. A61K 9/36
[52] U.S. Cl. .................................. 424/480; 424/476; 424/482
[58] Field of Search .................. 424/480, 476, 482

[56] References Cited

U.S. PATENT DOCUMENTS

| | | | |
|---|---|---|---|
| 4,140,756 | 2/1979 | Gallian | 424/21 X |
| 4,252,786 | 2/1981 | Weiss et al. | 424/19 |
| 4,309,406 | 1/1982 | Guley et al. | 424/21 |
| 4,459,279 | 7/1984 | Stricker et al. | 424/480 X |

FOREIGN PATENT DOCUMENTS

| | | |
|---|---|---|
| 0066505 | 12/1982 | European Pat. Off. . |
| 0158277 | 10/1985 | European Pat. Off. . |
| 1290661 | 3/1962 | France . |
| 84/02843 | 8/1984 | PCT Int'l Appl. .............. 424/480 |
| 8404674 | 12/1984 | PCT Int'l Appl. . |

OTHER PUBLICATIONS

Chemical Abstracts 86:95946a, 1977.
Kallstrand, Goran et al., *Membrane-Coated Tablets: A System for the Controlled Release of Drugs*, Jun. 28, 1982.

*Primary Examiner*—Michael Lusignan
*Attorney, Agent, or Firm*—George M. Gould; Bernard S. Leon; Dennis P. Tramaloni

[57] ABSTRACT

Pharmaceutical compositions for controlled release of water soluble drugs are disclosed. The compositions comprise a tablet core containing the drug and a water insoluble polymeric matrix surrounded with a rate controlling membrane coating.

10 Claims, 1 Drawing Sheet

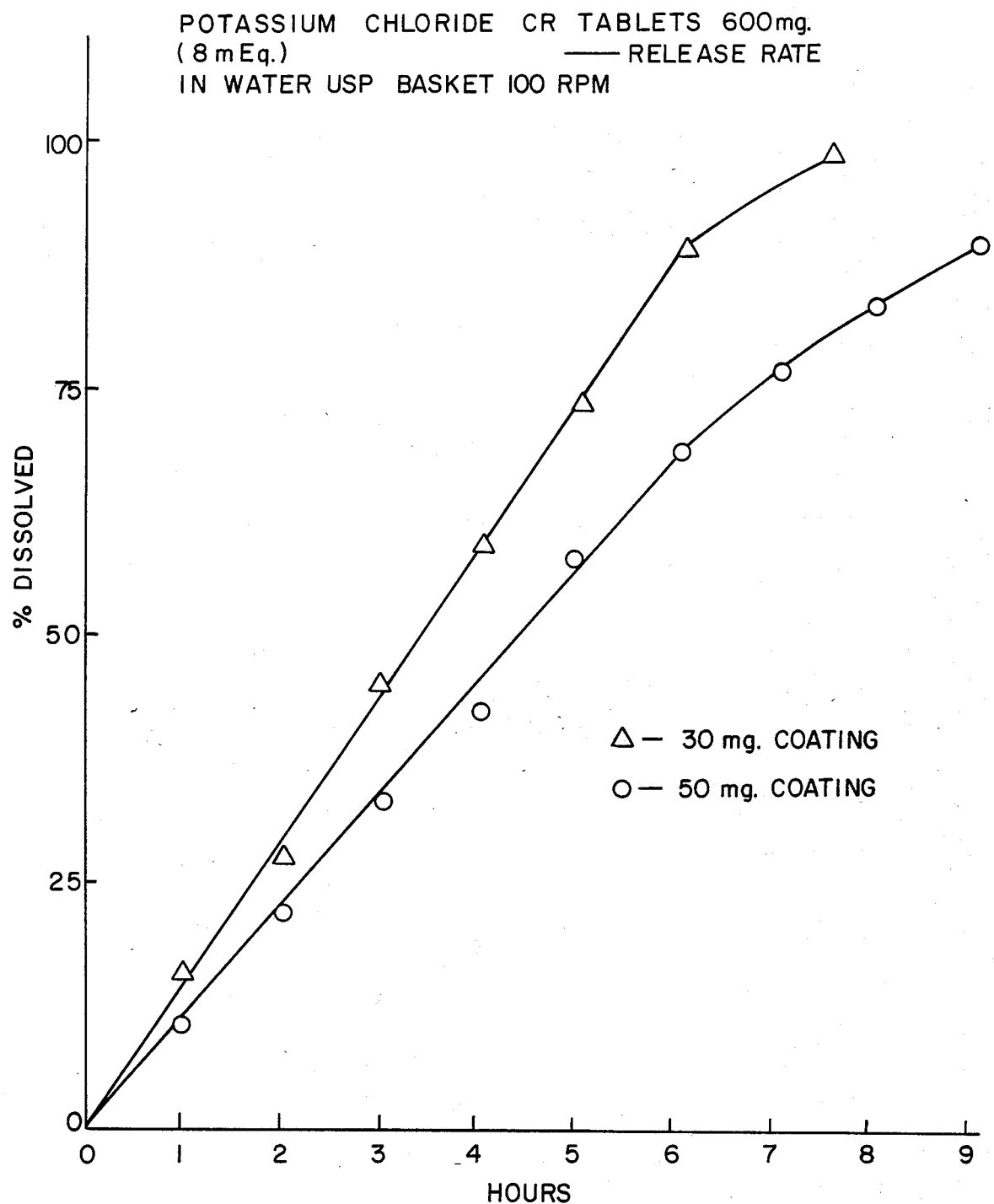
F I G. 1

CONTROLLED RELEASE COMPOSITIONS WITH ZERO ORDER RELEASE

SUMMARY OF THE INVENTION

According to the present invention, a controlled release composition is provided comprising a table core containing a water soluble active ingredient in a water insoluble polymeric matrix surrounded with a rate controlling membrane coating. The composition releases the active ingredient at a slow and constant rate through the membrane coated insoluble polymeric matrix.

BRIEF DESCRIPTION OF THE DRAWING

FIG. 1 shows the release rate with an 8% by weight of the polymeric membrane coating.

DETAILED DESCRIPTION OF THE INVENTION

In accordance with the present invention, formulations for the preparation of controlled release compositions for oral administration are provided, the controlled release compositions of the present invention consists of a tablet core component comprising a water soluble active ingredient in a water insoluble polymeric matrix surrounded with a rate controlling membrane coating.

The controlled release compositions of this invention comprises from about 85% to about 95% by weight of the tablet core component and from about 5% to about 15% by weight of a membrane coating. The tablet core comprises from about 5% to about 95% by weight of an active ingredient or drug and from about 5% to about 95% by weight of a water insoluble polymeric matrix.

The insoluble polymeric matrix of the table core of the present invention is sufficiently strong to retard the rate of release of the active ingredient or drug from the core. In addition, the tablet core provides a backbone for the outer rate controlling membrane. The polymeric matrix core prevents shrinkage and rupture of the membrane coating on exposure to gastrointestinal fluid. It also provides a tortuous path for penetrating gastrointestinal fluid, thereby keep a drug reservoir in the membrane coated polymeric matrix for a longer period of time.

Insoluble polymeric materials that can be suitably employed as the core matrix of this invention include ethyl cellulose, zein, and the like as well as mixtures thereof. Preferred polymeric materials include ethyl cellulose having a viscosity range of from about 3–100 cps and an ethoxy content of about 45 to 49.5%.

In addition to the polymeric material, the core matrix optionally may also contain a oil or wax-like material as plastisizers. Incorporation of the oil or wax-like material is useful for altering the release rates of the composition. Addition of the was also allows incorporation of higher concentrations of the active ingredient or drug into the formulation. Suitable oil or wax-like materials useful in the present invention include fatty acids such as stearic acid; long chain fatty alcohols such as, stearyl alcohol, cetyl alcohol, carnuba wax, beeswax, white wax, and the like. Suitable oils include vegetable oil and glycerides of $C_6$–$C_{18}$ fatty acids, mineral oil, triacetin dibutyl phthalate, dibutyl sebacate, triethyl citrate, and the like.

The polymeric matrix core formulation may further contain other pharaceutically acceptable excipients such as binders, fillers, stabilizers, compression aids, lubricants, granulation aids, flow aids, and the like. The choice of such materials and the amounts to be utilized are considered to be within the purview of one skilled in the art. It is possible to utilize the selection of inert pharmaceutical excipients to modify the rate of release of the formulation. For example, soluble excipients, for example, lactose, sucrose, mannitol, dextrose, sorbitol and the like will increase the rate of release of the active ingredient, whereas insoluble excipients, for example, calcium sulfate, barium sulfate, mono-, di- or tribasic calcium phosphate and the like will decrease the rate from the matrix.

The membrane coating is selected from one or more film forming materials which is capable of controlling the release of the drug out of the formulation. Examples of polymers that can be suitably employed as membrane coatings in accordance with the invention include ethyl cellulose, and mixtures of ethyl cellulose and hydroxypropyl cellulose, or hydroxypropyl methyl cellulose. A preferred membrane coating is ethyl cellulose having a viscosity range of from about 4-100 cps and an ethoxy content of about 45 to 49.5% and hydroxypropyl methyl cellulose having a methoxy percent of 16.5% to 32%, hydroxypropyl percent of about 4 to 33%, a methoxy degree of substitution between 1.12 to 2.03, and a viscosity range of from about 3 to 100,000 cps.

In order to minimize hardening and rupture of the membrane coating, it is often desirable to utilize a plasticizer in combination with the polymeric coating material. Examples of plasticizers that can be used in accordance with the invention include: triacetin, propylene glycol, polyethylene glycol having a molecular weight of about 200 to about 1,000, dibutyl phthalate, dibutyl sebacate triethyl citrate, vegetable and mineral oils, fatty acids, fatty acid glycerides of $C_6$–$C_{18}$ fatty acids, and the like. The membrane coating may further contain other coating excipients such as opacifiers, pigments, colorants and the like. The choice of such materials and the amounts to be utilized are considered to be within the purview of one skilled in the art.

The controlled release formulations of the present invention are prepared by techniques well established in the art. In most instances, formation of the core component, it is necessary to utilize the technique of wet granulation of allowed by compression into the core tablets. However, where the physical properties of the ingredients will permit, tablets may be prepared by direct compression of a homogeneous mixture of the ingredients. The core element prepared in accordance with the present invention can be manufactured on conventional tabletting equipment or molding equipment.

Application of the membrane coating to the core matrix is carried out by techniques well known in the art, such as pan coating fluid bed coating, etc.

The composition of this invention is suitable for drugs and other active ingredients which are water soluble. The composition is especially suitable for potassium chloride. The composition is also suitable for the following drugs: cibenzoline succinate, psuedoephedrine hydrochloride, chlorocitric acid, procainamide, theophylline.

The composition of this invention provides substantially zero order release of the core contained drug.

The invention is further illustrated but not limited by the following examples.

EXAMPLE 1

A controlled release composition containing potassium chloride was prepared as follows:

| Ingredients | mg/tablet |
|---|---|
| Potassium chloride | 600 |
| Ethyl cellulose | 100 |
| Neobee M5 (Medium chain triglyceride) | 35 |
| Magnesium stearate | 3 |
| | 738 mg |

The ethyl cellulose and Neobee M5 were dissolved in 10% of weight ethanol and potassium chloride than granulated. The granulation mixture was dried at 55° C. to a moisture content less than 2%. The mixture was screened and mixed with magnesium stearate, and then compressed into tablets.

The tablet core was coated with a polymeric membrane having the following composition:

| Ingredients | |
|---|---|
| Ethyl cellulose 50 cps | 3 |
| Hydroxypropyl methyl cellulose | 2 |
| Stearic acid | 1 |
| Methylene chloride | 47.5 |
| Alcohol | 47.5 |
| | 100.0 |

The film coating was applied to an approximate weight incorporation of 5-8% by weight of the final table weight.

The dissolution rate was run in simulated gastrointestinal fluid by UPS basket at 100 RPM. FIG. 1 shows the release rate with an 8% by weight of the polymeric membrane coating. An average of 11% was released per hour. The release characteristics are shown in Table I.

EXAMPLE 2

A controlled release composition containing potassium chloride was prepared as follows:

| Ingredients | |
|---|---|
| Potassium chloride | 600 |
| Ethocel (micromesh) | 80 |
| Ethocel | 20 |
| Stearic acid | 5 |
| Magnesium stearate | 3 |
| | 703 mg |

The potassium chloride and Ethocel (micromesh) were thoroughly mixed and granulated with the Ethocel and stearic acid in 10% by weight ethanol. The granulation was dried overnight at 55° C. The dried granulation was screened and mixed with stearic acid and magnesium stearate. The composition was compressed into tablets.

The tablet core was coated with a polymeric membrane having the following composition:

| Ingredients | % By Weight |
|---|---|
| Ethocel 10 cps | 3 |
| Methyl cellulose E15 | 2 |
| Dibutyl sebacate | 1 |
| Methylene chloride | 47.5 |
| Alcohol | 47.5 |
| | 100.0 |

The coating was applied to an approximate weight incorporation of 5-8% by weight of the final tablet weight.

The release characteristics was determined in the same manner as in Example 1 and are shown in Table I.

EXAMPLE 3

A controlled release composition containing potassium chloride was prepared as follows:

| Ingredients | mg/tablet |
|---|---|
| Potassium chloride | 1500 |
| Ethocel 50 cps | 80 |
| Stearic acid | 40 |
| Magnesium stearate | 3 |

The potassium chloride and a portion of the Ethocel and stearic acid were thoroughly mixed and granulated with a solution of the remainder of the Ethocel and stearic acid. The granulation was dried at 55° C. and the dried material passed through a #18 mesh screen. The magnesium stearate was added to the screened material and the composition was compressed into tablets. The compressed Tablets were heated at 76° C. in an oven for two (2) hours.

The table core was coated with, a polymeric membrane having the following composition:

| Ingredients | % By Weight |
|---|---|
| Ethocel 50 cps | 3 |
| Methocel E 15 | 2 |
| Neobee M5 (Medium chain triglyceride) | 1 |
| Methylene chloride | 47.5 |
| Alcohol | 47.5 |
| | 100.0 |

The coating was applied to an approximate weight incorporation of 5% by weight of the final tablet weight.

The release characteristics was determined in the same manner as in Example 1 and are shown in Table I.

EXAMPLE 4

A controlled release composition containing potassium chloride was prepared as follows:

| Ingredients | |
|---|---|
| Potassium chloride | 600 |
| Ethyl cellulose 50 cps | 50 |
| Dibutyl sebacate | 15 |
| Stearic acid | 5 |
| Magnesium stearate | 3 |

Micronized potassium chloride was granulated with a solution of Ethocel and dibutyl sabacate in 10% by weight ethanol. The dried material was screened through a #18 mesh screen. The stearic acid and magnesium stearate were added to the screened material and the composition compressed into tablets.

The table core was coated with a polymeric membrane having the following composition:

| Ingredients | % By Weight |
|---|---|
| Ethocel 50 cps | 3 |
| Methocel E 5 | 1 |
| Neobee M5 | 1 |
| Methylene chloride | 47.5 |
| Magnesium stearate | 47.5 |
| | 100.0 |

The coating was applied to an approximate weight incorporation of 5–8% by weight of the final tablet weight.

The release characteristics was determined in the same manner as in Example 1 and are shown in Table I.

TABLE I

Potasium Chloride constant Release Tablets Release rate in water USP Basket 100 RPM

| Example | Coating Applied | % Released | | | | | | | | |
|---|---|---|---|---|---|---|---|---|---|---|
| | | 1 hr | 2 hr | 3 hr | 4 hr | 5 hr | 6 hr | 7 hr | 8 hr | 9 hr |
| Example 1 | 5 | 15 | 31 | 44 | 61 | 74 | 87 | 96 | — | — |
| | 8 | 11 | 21 | 32 | 43 | 54 | 65 | 75 | 87 | 94 |
| Example 2 | 5 | 14 | 28 | 41 | 55 | 72 | 82 | 91 | 95 | — |
| | 8 | 10 | 21 | 30 | 41 | 51 | 60 | 71 | 82 | 89 |
| Example 3* | 5 | 8 | 16 | 25 | 32 | 41 | 49 | 56 | 66 | 74 |
| Example 4 | 5 | 9 | 18 | 26 | 35 | 45 | 55 | 64 | 74 | 82 |

*Release rate was run at different pHs showing Release rate is independent of pH.

I claim:

1. A controlled release composition in table form comprising
   (1) a core element comprising a 90–95% by weight of the tablet, said core comprising
      (a) 65–95% by weight of a water soluble active ingredient
      (b) 5–35% by weight of a water insoluble polymeric matrix; and
   (2) a membrane coating comprising 5–10% by weight of the tablet said membrane comprising a rate controlling polymer.

2. The composition of claim 1 wherein the insoluble polymeric matrix comprises a polymer selected from the group consisting of ethyl cellulose, and zein.

3. The composition of claim 2 wherein the polymeric matrix is a ethyl cellulose polymer.

4. The composition of claim 2 wherein the insoluble polymer matrix further contains an oil or wax-like material.

5. The composition of claim 4 wherein the oil or wax-like material comprises a member selected from the group consisting of stearic acid, stearyl alcohol, cetyl alcohol, fatty acids, long chain fatty alcohols, carnuba wax, beeswax, white wax, vegetable oil and fatty acid glycerides of $C_6$–$C_{18}$ fatty acids.

6. The composition of claim 5 wherein the membrane coating is selected from the group consisting of ethyl cellulose and mixtures of ethyl cellulose and of hydroxypropyl methylcellulose or hydroxypropyl cellulose.

7. The composition of claim 6 wherein the membrane coating is ethyl cellulose.

8. The composition of claim 6 wherein the membrane coating further contains a plasticizer.

9. The composition of claim 6 wherein the plasticizer is selected from the group consisting of triacetin, propylene glycol, polyethylene glycol having a molecular weight of 200 to 800, dibutyl phthalate, dibutyl sebacate, fatty acid, vegetable oils and glycerides of $C_6$–$C_{18}$ fatty acids.

10. The composition of claim 9 wherein the plasticizer is a triglyceride of $C_6$–$C_{10}$ fatty acid.

* * * * *